United States Patent [19]

Bennett

[11] Patent Number: Plant 5,590

[45] Date of Patent: Dec. 10, 1985

[54] MINIATURE ROSE PLANTS

[76] Inventor: Cecilia L. D. Bennett, 489 Minot Ave., Chula Vista, Calif. 92010

[21] Appl. No.: 200,200

[22] Filed: Aug. 1, 1983

[51] Int. Cl.[4] ..... A01H 5/00

[52] U.S. Cl. ..... Plt./7

[58] Field of Search ..... Plt./7, 9

*Primary Examiner*—Robert E. Bagwill

[57] ABSTRACT

The subject of the present disclosure is a new and distinct variety of miniature rose plant characterized by the delicate blending of yellow, pink and apricot plus the long slender buds on long slender stems.

1 Drawing Figure

The present invention relates to a new and distinct variety of a bush type rose plant of miniature class; the variety showing a resemblance in color to Elizabeth of Glamis. (U.S. Plant Pat. No. 2,721).

The variety is further characterized by:

An abundance of long slender buds held erect on long slender stems. One to a stem.

Has a very faint fragrance.

The plant is very compact and erect. The foliage is medium green; the buds and flowers are a soft shell pink, with soft yellow at the base, often showing a strong apricot tendancy. Blooms do not reflex so retain their beauty for at least a week.

The plant ranges in size from 12–18 inches.

The plant has good growing habits. Repeat blooms with very little assistance. A very attractive plant.

The present variety of miniature rose originated by me at Tiny Petal's Nursery, located at Chula Vista, Calif., under careful observation, and is a cross of Little Darling (U.S. Plant Pat. No. 1,581) a floribunda as the seed parent and Over the Rainbow, a miniature (U.S. Plant Pat. No. 3,472) the pollen parent.

Subsequent to origination of the variety I successfully reproduced at Tiny Petal's Nursery located at aforesaid with reproduction coming true in all respects.

The color photographs illustrate the variety.

Referring now specifically to the new and distinct variety of miniature rose plant, the following is a detailed description therefore in outline; all major color plate identifications being by reference to Wilson's Horticultural Colour Chart.

Type: Hardy; seedling; greenhouse; potted plant; garden decoration; cut flowers; exhibition.

Class:

*Miniature.*—Variety name "Tiffie".

Flowers borne: Usually one to a stem on long straight slender stems.

Quantity of bloom: Usually abundant both inside and outside of the greenhouse.

Bud:

*Peduncle.*—Medium to long; slender; erect; reddish-green.

*Before calyx breaks; size.*—Small. Form long and slender. Few foliaceous appendages and numerous minute hairs on surface of the bud; with foliaceous parts extending beyond the tip of the bud equal to one quarter of an inch.

*Color.*—Medium green with a faint tinge of red.

*As calyx breaks, color.*—Soft shell pink. Opens to a soft apricot similar to 609 (Wilson). Yellow at the base of the petals. Opening: opens well in all weather.

Bloom:

*Size when fully open.*—Small, averaging about 1" to 1¼".

*Petalage.*—Double — Averaging about 15 to 20 petals, arranged regularly.

*Form.*—High centered, opening slowly with a slight roll on the outer petals. Exhibition form. Flower opens slowly to show stamens.

Petals: Good substance; satiny surface.

*Shape.*—Outside petals; broad lanceolate with slight acute tip; Intermediate-Medium lanceolate with rounded tip, inside petals — Small arrow shaped.

Color: Newly opened flower from a flower grown outside, Chula Vista, Calif.:

Outside petals:

*Outside surface.*—Soft shell pink, 516/3 (Wilson) with soft yellow base of petal.

*Inside surface.*—Soft shell pink with soft yellow at the base of petal.

Intermediate petal: Outside and inside petal surface a soft apricot.

Inner petal: Outside and inside petals, a deeper shade of apricot near 516/3 (Wilson).

General color effect:

*Newly opened flowers.*—Soft shell pink blending to an apricot center.

*Third day open.*—Slightly paler.

Behavior: Opens well in all weather. Flowers fade to a shell pink by the end of one week. Bloom keeps upright appearance.

Reproductive organs:

*Stamens.*—Abundant, arranged evenly around pistils.

*Filaments.*—Short, yellow, varying lengths.

*Anthers.*—Well shaped: yellow.

*Pollen.*—A lot.

*Pistils.*—A lot.

*Styles.*—Even: greenish.

*Ovaries.*—All encased in calyx.

*Seed.*—A few.

Foliage:

*Leaves.*—Compound of five with an occasional seven.

*Leaflets.*—Fairly small: Semi-glossy, broad, apex acute, base tapered, margin serrated.

*Color.*—Medium green with red on outer leaflets of newer foilage.

*Rachis.*—Medium green; medium length; upperside grooved; underside has a lot of minute prickles.

*Stiples.*—Medium length; medium width; short which curve outward.

Growth:

*Habit.*—Dwarf; spreading but compact; much branched.

*Growth.*—Free vigorous;

*Canes.*—Long; slender and straight.

*Main stems.*—Color: medium green.

*Thorns.*—None.

*Prickles.*—None.

*Hairs.*—None.

Branches:

*Color.*—Medium green with reddish green on younger branches. Thorns: none. Prickles: none: Hairs: none.

The miniature rose described herein and its flowers may vary in slight detail due to climatic, soil and cultural conditions under which the variety may be grown; the present description being of the variety grown at Chula Vista, Calif.

The following is claimed:

1. A new and distinct variety of miniature rose plant, substantially as shown and described, characterized by buds and blossoms of a soft shell pink color, with varying amounts of apricot, similar to Elizabeth of Glamis, being borne singly on long, slender, thornless stems, the plant being dwarf, hardy, rounded, much branched, well foliaged, vigorous, and easily propagated from buds or cuttings.

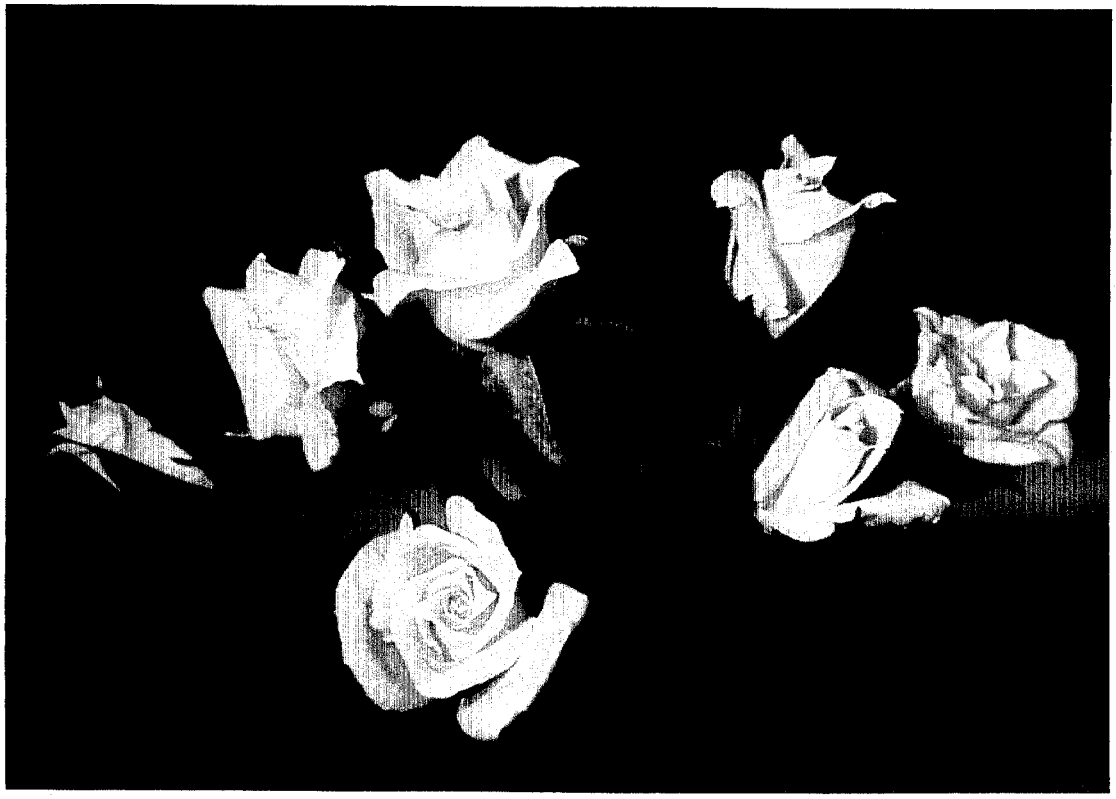

* * * * *